US012708265B2

(12) United States Patent
Lee et al.

(10) Patent No.: US 12,708,265 B2
(45) Date of Patent: Aug. 18, 2026

(54) BIOPROCESSING ELEMENT AND NEURAL NETWORK PROCESSOR WITH BIOPROCESSING ELEMENT

(71) Applicant: Samsung Electronics Co., Ltd., Suwon-si (KR)

(72) Inventors: Hankyu Lee, Suwon-si (KR); Sang Joon Kim, Hwaseong-si (KR); Chisung Bae, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 1165 days.

(21) Appl. No.: 17/591,206

(22) Filed: Feb. 2, 2022

(65) Prior Publication Data

US 2022/0414435 A1 Dec. 29, 2022

(30) Foreign Application Priority Data

Jun. 24, 2021 (KR) ........................ 10-2021-0082497

(51) Int. Cl.

| | |
|---|---|
| ***A61B 5/00*** | (2006.01) |
| ***A61B 5/024*** | (2006.01) |
| ***A61B 5/369*** | (2021.01) |
| ***G06N 3/04*** | (2023.01) |
| ***G06N 3/06*** | (2006.01) |

(52) U.S. Cl.

CPC ................ *A61B 5/00* (2013.01); *A61B 5/369* (2021.01); *G06N 3/04* (2013.01); *G06N 3/061* (2013.01)

(58) Field of Classification Search

CPC ........... A61B 5/24; A61B 5/369; A61B 5/291; A61B 5/4094; A61B 5/372; A61B 5/293; A61B 5/0031; A61B 5/0006; A61B 2562/046; A61B 5/6868; A61B 5/686; A61B 5/30; A61B 5/6814; A61B 5/287; A61B 5/282; A61B 5/37; A61B 5/4893;

(Continued)

(56) References Cited

U.S. PATENT DOCUMENTS

2005/0090756 A1* 4/2005 Wolf ........................ A61B 5/30 607/48

2011/0054583 A1* 3/2011 Litt ........................ A61B 5/291 600/377

(Continued)

FOREIGN PATENT DOCUMENTS

CN 102178999 B 6/2013
CN 106022207 B 12/2019

(Continued)

OTHER PUBLICATIONS

Noshahr et al. "Multi-Channel Neural Recording Implants: A Review" Sensors: Feb. 2020, 20, 904. (Year: 2020).*

(Continued)

*Primary Examiner* — Joseph A Stoklosa
*Assistant Examiner* — Brian M Antiskay
(74) *Attorney, Agent, or Firm* — NSIP Law

(57) ABSTRACT

A bioprocessing device performing an operation based on cultured biological neurons includes: an electrode layer comprising electrodes connected to the biological neurons;

(Continued)

circuit layers, stacked with the electrode layer, comprising stacked circuits for the biological neurons; and inter-layer connectors configured to connect the electrode layer and the circuit layers.

26 Claims, 5 Drawing Sheets

(58) Field of Classification Search
CPC ........ A61B 5/304; A61B 5/29; A61N 1/0551; A61N 1/05; A61N 1/0534; A61N 1/0529
USPC ................ 600/372–373, 377–378, 544–545; 607/115–118
See application file for complete search history.

(56) References Cited

U.S. PATENT DOCUMENTS

| | | | | |
|---|---|---|---|---|
| 2015/0276430 | A1* | 10/2015 | Sekitani ................ | G06F 3/0445 324/609 |
| 2017/0337469 | A1* | 11/2017 | Debes .................... | G06N 3/049 |
| 2018/0046900 | A1 | 2/2018 | Dally et al. | |
| 2019/0164038 | A1 | 5/2019 | Zhang | |
| 2020/0292482 | A1 | 9/2020 | Ham et al. | |

FOREIGN PATENT DOCUMENTS

| | | | |
|---|---|---|---|
| CN | 111569252 | A | 8/2020 |
| KR | 10-2009-0081266 | A | 7/2009 |
| KR | 10-2021-0050966 | A | 5/2021 |

OTHER PUBLICATIONS

Abbott, Jeffrey, et al. “A nanoelectrode array for obtaining intracellular recordings from thousands of connected neurons.” *Nature biomedical engineering vol. 4 Issue 2* Feb. 2020 pp. 232-241.

Abbott, Jeffrey, et al. “The Design of a CMOS Nanoelectrode Array With 4096 Current-Clamp/Voltage-Clamp Amplifiers for Intracellular Recording/Stimulation of Mammalian Neurons.” *IEEE Journal of Solid-State Circuits vol. 55 Issue 9*Sep. 2020 pp. 2567-2582.

Wendler, Daniel, et al. “28.7 A 0.00378 mm 2 Scalable Neural Recording Front-End for Fully Immersible Neural Probes Based on a Two-Step Incremental Delta-Sigma Converter with Extended Counting and Hardware Reuse.” *IEEE International Solid-State Circuits Conference (ISSCC) vol. 28 Issue 7*, Feb. 18, 2021 pp. 398-400.

Korean Office Action Issued on Apr. 14, 2025, in Counterpart Korean Patent Application No. 10-2021-0082497 (4 Pages in English, 12 Pages in Korean).

* cited by examiner

BIOPROCESSING ELEMENT AND NEURAL NETWORK PROCESSOR WITH BIOPROCESSING ELEMENT

CROSS-REFERENCE TO RELATED APPLICATIONS

This application claims the benefit under 35 USC § 119(a) of Korean Patent Application No. 10-2021-0082497, filed on Jun. 24, 2021 in the Korean Intellectual Property Office, the entire disclosure of which is incorporated herein by reference for all purposes.

BACKGROUND

1. Field

The following description relates to a bioprocessing element and a neural network processor including bioprocessing elements.

2. Description of Related Art

Neuromorphic engineering may include the use of analog integrated circuits to implement neural network structures and functions of a biological nervous system and further may include, for example, the use of integrated circuits to fully implement the structures and functions of the brain in an electronic system, as well as to understand some operating principles of the brain and implement a system applying the same.

A neuromorphic electronic device may be classified as a natural neural network (NNN) aiming to copy a natural neural network of the brain and an artificial neural network (ANN) converting an operating principle of unit cells of the brain into a simplified mathematical model. To copy human intelligence by a natural neural network, it may be necessary to identify an operation mechanism of a neuron which is a unit component of the brain, and a structure and feature of a neural network connected to a plurality of neurons. However, doing this is exceedingly difficult.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a bioprocessing device performing an operation based on cultured biological neurons includes: an electrode layer comprising electrodes connected to the biological neurons; circuit layers, stacked with the electrode layer, comprising stacked circuits for the biological neurons; and inter-layer connectors configured to connect the electrode layer and the circuit layers.

An area of each of the circuit layers may be smaller than or equal to an area of the electrode layer.

An area of the electrode layer may be determined based on either one or both of a thickness of the inter-layer connectors and a number of the inter-layer connectors.

Any one or any combination of any two or more of a number of the electrodes, a number of the circuit layers, a circuit configuration of each of the circuit layers, and a method of connection between the circuit layers may be determined based on an application field of the device.

A disposition spacing between the electrodes may be determined based on a size of the biological neurons.

The inter-layer connectors may include either one or both of: through silicon vias (TSVs) penetrating the electrode layer and the circuit layers; and micro bumps connecting the electrode layer and the circuit layers.

Each of the circuit layers may include blocks configured to perform a predetermined function, and signals of blocks performing a same function among the blocks comprised in the corresponding circuit layer may be grouped into one group and transmitted.

Each of the blocks may include a circuit configured to perform a predetermined function.

The blocks performing the same function among the blocks may be contiguously disposed to each other.

Each of the circuit layers may include blocks configured to perform a predetermined function, and signals of at least a portion of the blocks comprised in a corresponding circuit layer may be grouped through circuits connected to the inter-layer connectors.

Each of the circuit layers may include blocks configured to perform a predetermined function, and one or more of the blocks may receive a signal from one or more of the electrodes.

Each of the circuit layers may include blocks configured to perform a predetermined function, and signals of at least a portion of the blocks comprised in a corresponding circuit layer may be grouped by any one or any combination of any two or more of a time division multiplexing method, a frequency division multiplexing method, and a code division multiplexing method.

The circuit layers may include blocks configured to perform a predetermined function, and, in response to functionally contiguous blocks among the blocks being dispersed to different circuit layers, the dispersed blocks may be interconnected by the inter-layer connectors.

The device may be configured to perform either one or both of stimulating the biological neurons and analyzing a neural signal of the biological neurons.

The device may be a bioprocessing element.

A neural network processor may include a plurality of the bioprocessing device, wherein the bioprocessing devices are connected in parallel.

In another general aspect, a neural network processor includes: a plurality of bioprocessing devices performing an operation based on cultured biological neurons, wherein the bioprocessing devices are connected in parallel, and wherein each of the bioprocessing elements may include: an electrode layer comprising electrodes connected to the biological neurons; circuit layers, stacked with the electrode layer, comprising stacked circuits for the biological neurons; and inter-layer connectors configured to connect the electrode layer and the circuit layers.

A disposition spacing between the bioprocessing devices may be determined based on an electrode density of the electrodes.

Each of the circuit layers may include blocks configured to perform a predetermined function, and signals of blocks performing a same function among the blocks comprised in a corresponding circuit layer may be grouped into one group and transmitted.

Each of the circuit layers may include blocks configured to perform a predetermined function, and signals of at least a portion of the blocks comprised in a corresponding circuit layer may be grouped through circuits connected to the inter-layer connectors.

Each of the circuit layers may include blocks configured to perform a predetermined function, and one or more of the blocks receives a signal from one or more of the electrodes.

Each of the circuit layers may include blocks configured to perform a predetermined function, and signals of at least a portion of the blocks comprised in a corresponding circuit layer may be grouped by any one or any combination of any two or more of a time division multiplexing method, a frequency division multiplexing method, and a code division multiplexing method.

The circuit layers may include blocks configured to perform a predetermined function, and, in response to functionally contiguous blocks among the blocks being dispersed to different circuit layers, the dispersed blocks may be interconnected by the inter-layer connectors.

In another general aspect a bioprocessing device performing an operation based on cultured biological neurons includes: an electrode layer comprising electrodes connected to the biological neurons; a circuit layer stacked with the electrode layer and comprising groups of adjacent circuit blocks, wherein, for each of the groups, the circuit blocks of the group are configured to perform a same operation; and inter-layer connectors configured to connect the electrode layer and the circuit layer.

Circuit blocks of a first group of the groups may be configured to perform a first operation, and circuit blocks of a second group of the groups may be configured to perform a second operation.

The first operation and the second operation may correspond to different operations among measuring a neural signal of the biological neurons, processing the neural signal of the biological neurons, and providing a stimulus signal to the biological neurons.

Other features and aspects will be apparent from the following detailed description, the drawings, and the claims.

Figure 1:
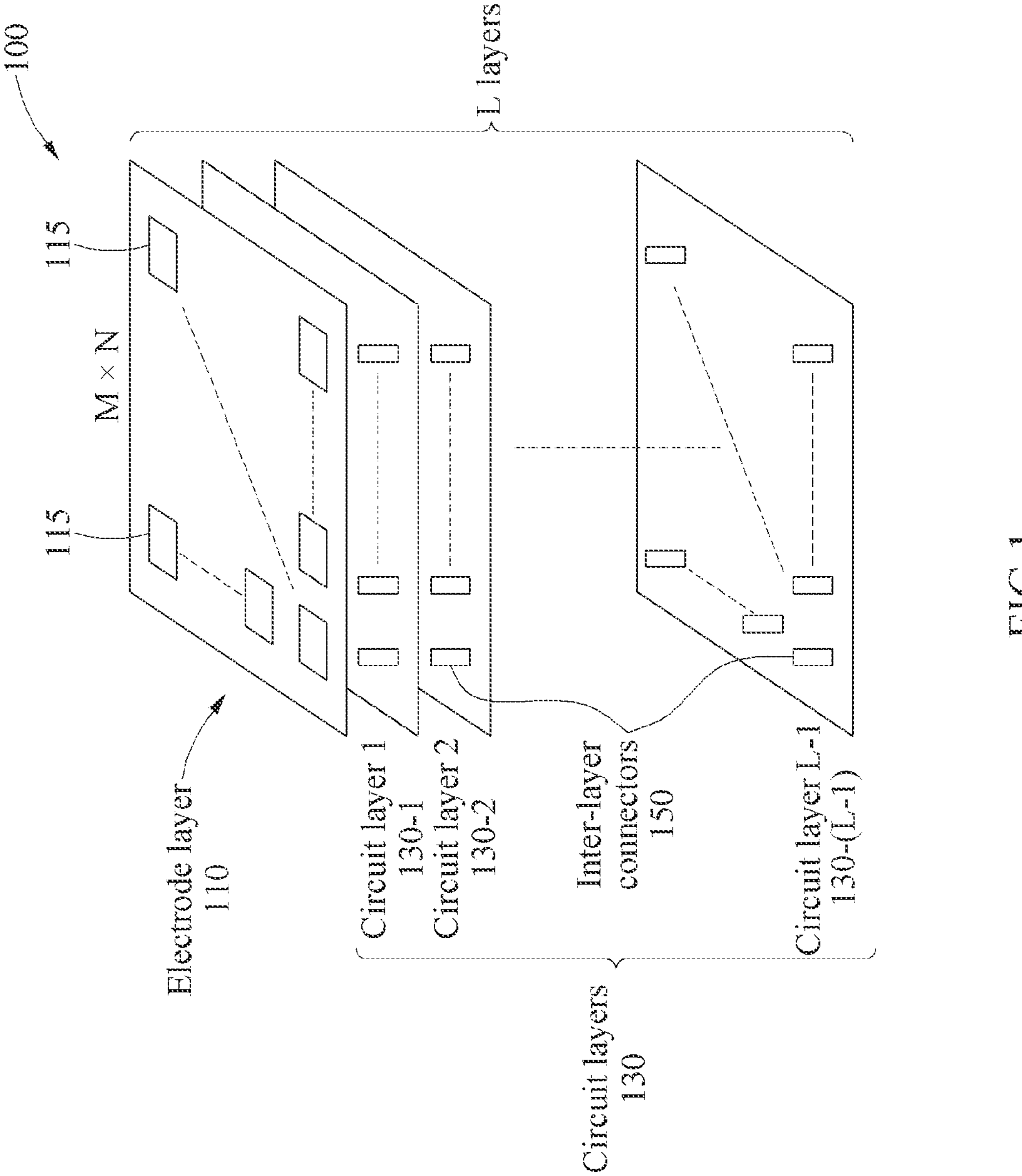
FIG. 1 illustrates an example of a structure of a bioprocessing element.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known, after an understanding of the disclosure of this application, may be omitted for increased clarity and conciseness.

Although terms of "first" or "second" are used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

Throughout the specification, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween. Likewise, expressions, for example, "between" and "immediately between" and "adjacent to" and "immediately adjacent to" may also be construed as described in the foregoing.

The terminology used herein is for the purpose of describing particular examples only, and is not to be used to limit the disclosure. As used herein, the singular forms "a", "an", and "the" are intended to include the plural forms as well, unless the context clearly indicates otherwise. As used herein, the term "and/or" includes any one and any combination of any two or more of the associated listed items. It will be further understood that the terms "comprises," "includes," and "has" specify the presence of stated features, numbers, integers, steps, operations, elements, components, and/or combinations thereof, but do not preclude the presence or addition of one or more other features, numbers, integers, steps, operations, elements, components, and/or combinations thereof. The use of the term "may" herein with respect to an example or embodiment (for example, as to what an example or embodiment may include or implement) means that at least one example or embodiment exists where such a feature is included or implemented, while all examples are not limited thereto.

Unless otherwise defined, all terms, including technical and scientific terms, used herein have the same meaning as commonly understood by one of ordinary skill in the art to which this disclosure pertains and based on an understanding of the disclosure of the present application. Terms, such as those defined in commonly used dictionaries, are to be interpreted as having a meaning that is consistent with their meaning in the context of the relevant art and the disclosure of the present application, and are not to be interpreted in an idealized or overly formal sense unless expressly so defined herein.

Hereinafter, example embodiments will be described in detail with reference to the accompanying drawings. When describing the example embodiments with reference to the accompanying drawings, like reference numerals refer to like components and a repeated description related thereto will be omitted.

FIG. 1 illustrates an example of a structure of a bioprocessing element (e.g., a bioprocessing device). More specifically, FIG. 1 illustrates a structure of a bioprocessing element 100 including an electrode layer 110, circuit layers 130, and inter-layer connectors 150.

The bioprocessing element 100 may perform an operation based on biological neurons cultured on the electrode layer 110. The bioprocessing element 100 may measure or record diverse bio-signals generated in interconnected biological neurons forming a neural network. The biological neurons may be living nerve cells, not artificial neurons. Hereinafter, the terms "neurons" and "nerve cells" may be understood to have the same meaning. Here, "operations based on the biological neurons" may include, for example, any one or any combination of any two or more of synaptic connection analysis, ion channel analysis, ion channel current measurement, and measurement of effects of drugs on network connections and dynamics. However, the examples are not limited thereto.

The electrode layer 110 may include electrodes 115 connected to the cultured biological neurons. The bioprocessing element 100 may record (or measure) neural signals generated in the biological neurons, and/or may inject (or provide) a stimulus signal to the biological neurons by contacting the biological neurons through the electrodes 115. A disposition spacing between the electrodes 115 may be determined based on a size of the biological neurons. The electrodes 115 may be disposed in a spacing, for example, of less than or equal to 20 μm, according to a size of the biological neurons such that neural signals may be easily stimulated or recorded.

The electrode layer 110 may be an electrode array configured to record electrophysiological activities of a plurality of biological neurons in parallel. The electrode layer 110 may be, for example, a complementary metal-oxide-semiconductor (CMOS) microelectrode array (MEA).

For example, the electrode layer 110 may identify a synaptic weight map between the biological neurons by recording and analyzing neural signals simultaneously entering from a plurality of channels of the biological neurons. The electrode layer 110 may be a "recording area" since it records the neural signals received from the plurality of channels of the biological neurons.

A functional map of the brain may be generated by recording (measuring) and/or analyzing neural signals generated in biological neurons of a large-scale neural network such as the brain, or a new structure of a neuromorphic processor may be developed through copying a brain.

The circuit layers 130 may include stacked circuits for the biological neurons and may be stacked with the electrode layer 110. Here, the stacked circuits may be, for example, circuits to perform a function (e.g., a predetermined operation) such as any one or any combination of any two or more of measuring a neural signal, processing a signal, and analyzing. The circuits having the above-mentioned functions may be implemented such that they are distributed to a number of circuit layers or integrated in one circuit layer. The circuits may be, for example, CMOS integrated circuits (ICs). However, the examples are not necessarily limited thereto. The circuit layers 130 may be vertically stacked with the electrode layer 110, and the circuits included in each of the circuit layers may also be vertically stacked with each other.

For example, the circuit layers 130 may include a circuit layer 1 130-1, a circuit layer 2 130-2, . . . , a circuit layer L−1 130-(L−1). Each of the circuit layers 130 may be vertically stacked with each other. Each of the circuit layers 130 may include circuits (e.g., of blocks) for performing a different function or operation. For example, the circuit layer 1 130-1 may include a circuit for multiplexing, the circuit layer 2 130-2 may include a circuit for filtering, and the circuit layer L−1 130-(L−1) may include a circuit for voltage amplification.

Alternatively, each of the circuit layers 130 may include circuits for performing the same functions or operations. For example, the circuit layer 1 130-1 may include a circuit for multiplexing, a circuit for filtering, a circuit for voltage amplification, and a clamping circuit for current injection, and the circuit layer 2 130-2 may also include a circuit for multiplexing, a circuit for filtering, a circuit for voltage amplification, and a clamping circuit for current injection like the circuit layer 1 130-1.

Each of the circuit layers 130 may include unit blocks to perform a predetermined function. Here, a "unit block", for example, may be a block corresponding to one functional unit, device, module, circuit, or portion to perform a predetermined function within a layer such as an electrode and a circuit, and may be referred to as a "unit pixel" or "pixel block". Non-limiting examples of the unit blocks will be described in further detail with reference to FIG. 2.

An area of each of the circuit layers 130 may be smaller than or equal to an area of the electrode layer 110. A total area used by a circuit for performing an operation based on biological neurons may be secured or set by adjusting a disposition spacing between the electrodes 115 based on a size (for example, smaller than or equal to the size of the biological neurons) of cultured biological neurons and vertically stacking layers (the electrode layer 110 and the circuit layers 130) to implement a recording channel using a large space.

In addition, a two-dimensional scalability may be secured while a high-density recording area is maintained by stacking the layers wherein the area of each of the circuit layers 130 does not exceed the area of the electrode layer 110.

The inter-layer connectors 150 may connect the electrode layer 110 and the circuit layers 130. The inter-layer connectors 150 may be, for example, either one or both of through silicon vias (TSVs) penetrating the electrode layer 110 and the circuit layers 130 and micro bumps connecting the electrode layer 110 and the circuit layers 130.

TSV is a packaging technique for drilling fine vias in chips and filling the vias with conductive materials to connect upper chips and lower chips, rather than connecting the chips using wires. Since the TSVs secure direct electrical connection paths in the chips and thus, do not require additional space, the package size may be reduced, and the length of interconnection between the chips may be reduced.

A total chip area used for implementing a sensor or a signal processor while a chip area does not exceed a recording area may be secured or set by vertically stacking each of the circuit layers 130 having an area smaller than or equal to an area of the electrode layer 110 through a three-dimensional stacking structure using TSV.

As shown in FIG. 1, the electrode layer 110 including an arbitrary number (for example, M×N) of the electrodes 115 (e.g., electrode pads) may be disposed at the uppermost layer of the bioprocessing element 100. Beneath the electrode layer 110, an arbitrary number (for example, L) of the circuit layers 130 (including ICs to perform, for example, any one or any combination of any two or more of measuring a neural signal, processing a signal, and analyzing) may be stacked. Connections such as signal, power, and clock connections between the electrode layer 110 and the circuit layers 130 may be provided by the inter-layer connectors 150 connecting the layers.

A thickness of the inter-layer connectors 150 may vary, for example, based on a feature of a signal transmitted through the corresponding inter-layer connector(s), a position of layers connected by the corresponding inter-layer connector(s), and/or a distance between layers connected by the corresponding inter-layer connector(s). For example, when an inter-layer connector is connected to a circuit layer configured to receive an input signal, a thickness of the corresponding inter-layer connector may be increased or may be large when the inter-layer connector is sensitive to noise by the input signal. In contrast, when an inter-layer connector is connected to a circuit layer configured to transmit an output signal, a thickness of the corresponding inter-layer connector may be decreased or may be small when the inter-layer connector is not affected or substantially affected by noise from the output signal.

When an inter-layer connector connects spaced apart layers (for example, a circuit layer 1 and a circuit layer 4), a length and a thickness of the corresponding inter-layer connector may be increased or may be large. Alternatively, when an inter-layer connector connects contiguous or immediately adjacent layers (for example, the circuit layer 1 and a circuit layer 2), a length and a thickness of the corresponding inter-layer connector may be decreased or may be small.

A number of the inter-layer connectors 150 may be determined based on a number of electrodes disposed in layers connected by the corresponding inter-layer connectors and/or a number of circuits disposed in layers connected by the corresponding inter-layer connectors.

For example, when a thickness or a number of the inter-layer connectors 150 increases, an area of layers included in the bioprocessing element 100 may be increased. An area of the electrode layer 110 and/or an area of the circuit layers 130 may be determined based on either one or both of the thickness of the inter-layer connectors 150 and the number of the inter-layer connectors 150.

For example, a circuit configuration of the bioprocessing element 100 may vary by application field, and accordingly, a type, a number, and a disposition of the ICs in use may vary. In the bioprocessing element 100, any one or any combination of any two or more of a number of the electrodes 115, a number of the circuit layers 130, a circuit configuration of each of the circuit layers 130, and a connection method between the circuit layers 130 may be determined based on an application field of the bioprocessing element 100.

Figure 2:
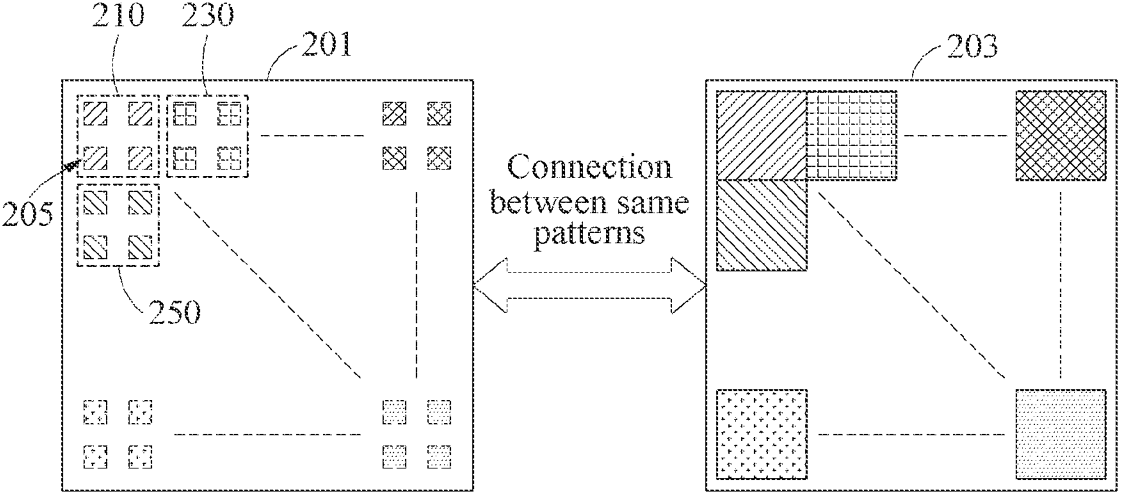
FIGS. 2 to 4 illustrate examples of methods of connection between contiguous layers within a bioprocessing element.

FIG. 2 illustrates an example of a method of connection between contiguous layers within a bioprocessing element. More specifically, FIG. 2 illustrates a circuit layer 201 including unit blocks (e.g., blocks each including) 205 performing a predetermined function (e.g., operation).

Rectangles shown in the illustration of circuit layer 201 may each represent one unit block 205 respectively. A pattern displayed on the unit block 205 may represent a function performed by the corresponding unit block. For example, unit blocks performing the same function may be expressed by the same pattern, and unit blocks performing different functions may be expressed by different patterns.

Although an area of each of layers may be minimized using an inter-layer connector (for example, TSV) penetrating the layers, a limitation in reducing an area of the unit block 205 may be present due to, for example, an area of inter-layer connectors, a spacing between the inter-layer connectors, and/or an area of a portion of a circuit to be necessarily placed on the same layer. Due to the limitation, when connecting layers, it may be difficult for all unit blocks in each layer to correspond respectively to inter-layer connectors or a one-to-one correspondence may be inefficient.

When all the unit blocks 205 in a layer are not connected respectively to inter-layer connectors for the above-described reason, an arbitrary number of the unit blocks 205 included in the circuit layer 201 may be grouped into one group and a signal of the grouped unit blocks may be transmitted to a circuit layer 203 contiguous to the circuit layer 201.

Among the unit blocks included in the circuit layer 201, unit blocks expressed in the same pattern may be connected through an inter-layer connector. In other words, signals of unit blocks performing a same function among the unit blocks included in the circuit layer 201 may be grouped (for example, block groups 210, 230, and 250) based on the function through inter-layer connectors, and may be transmitted to the next layer 203 contiguous to the circuit layer 201. Here, unit blocks forming each of the block groups 210, 230, and 250 performing the same function among the unit blocks included in the circuit layer 201 may be contiguously disposed in the circuit layer 201. By grouping the unit blocks, a size of the unit blocks may be, for example, advantageously expanded by four times in the circuit layer 203, compared to a typical bioprocessing element.

Figure 3:
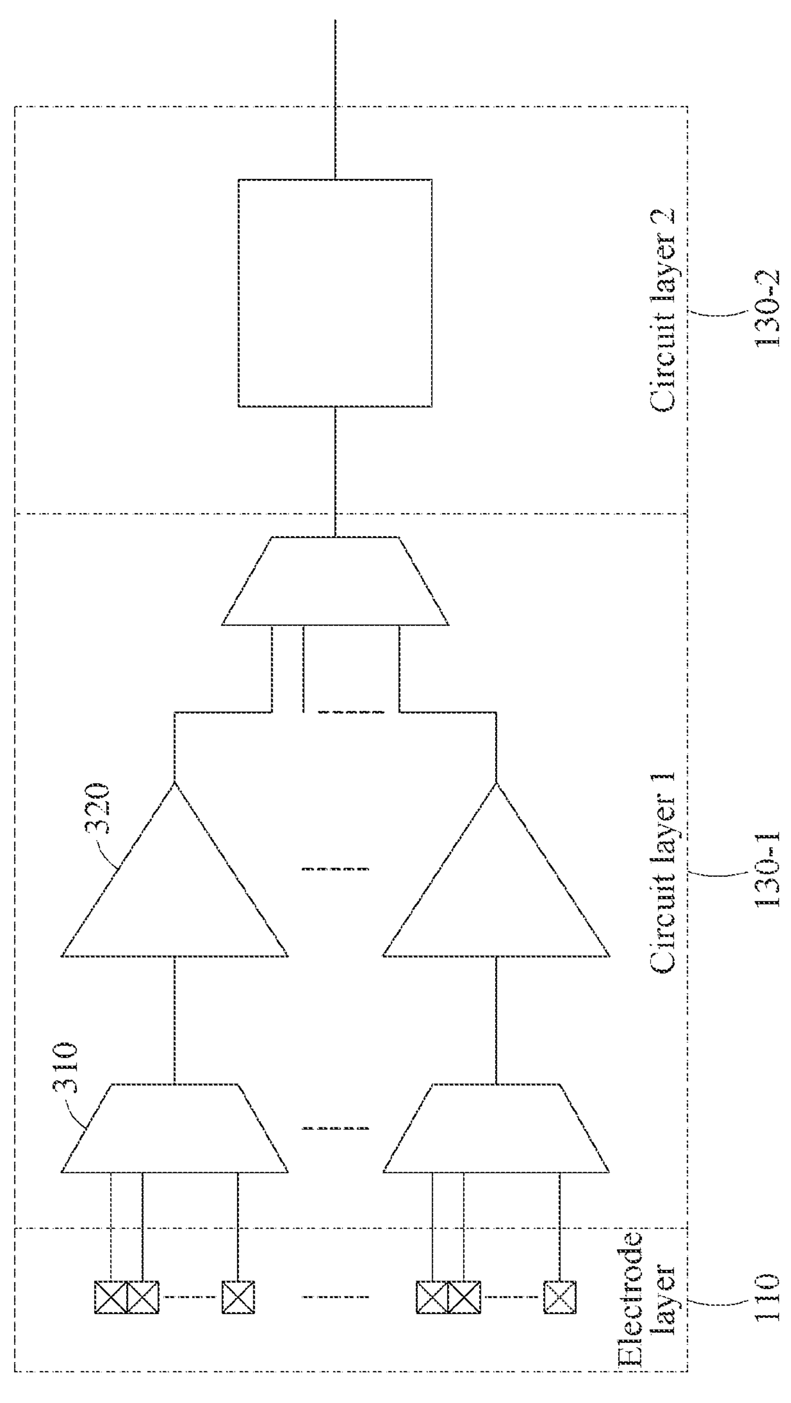

FIG. 3 illustrates an example of a method of connection between contiguous layers within a bioprocessing element. More specifically, FIG. 3 illustrates an example of grouping and connecting an input signal and output signal of a portion of unit blocks when connecting layers in a bioprocessing element, instead of one-to-one correspondences of the input signal and output signal of all unit blocks in each layer to inter-layer connectors.

Here, in grouping an input signal and output signal of at least a portion of unit blocks, for example, a circuit, such as a multiplexer 310, a buffer 320, and a switch may be used, however, the examples are not limited thereto. One or more of the unit blocks may receive a signal from one or more of electrodes in the electrode layer 110.

For example, when there is a high level of complexity in a circuit of the circuit layer 1 130-1 of the bioprocessing element, it may be difficult to dispose one unit block of the circuit layer on one electrode. In this case, as an input end of the circuit layer 1 130-1, one unit block may be configured to receive an input signal from a plurality of electrodes of the electrode layer 110.

For example, to reduce a number of inter-layer connectors used in the bioprocessing element, similar to a configuration of an output end of the circuit layer 1 130-1, inputs or outputs of a plurality of unit blocks may be bundled into one signal and transmitted to the next layer (for example, the circuit layer 2 130-2).

Signals of at least a portion of the unit blocks included in the corresponding circuit layer may be grouped by any one or any combination of any two or more of a time division multiplexing method, a frequency division multiplexing method, and a code division multiplexing method.

For example, when a unit block of the circuit layer 1 130-1 receives input signals (e.g., input signal 1, 2, 3 and 4) from four electrodes of the electrode layer 110, signals input to the unit block may be grouped signals of the signals transmitted from the four electrodes. Here, the grouped signals may be sequentially transmitted to the unit block with the input signal 1 at 0.1 second, the input signal 2 at 0.2 second, the input signal 3 at 0.3 second, and the input signal 4 at 0.4 second according to the time division multiplexing method.

Figure 4:
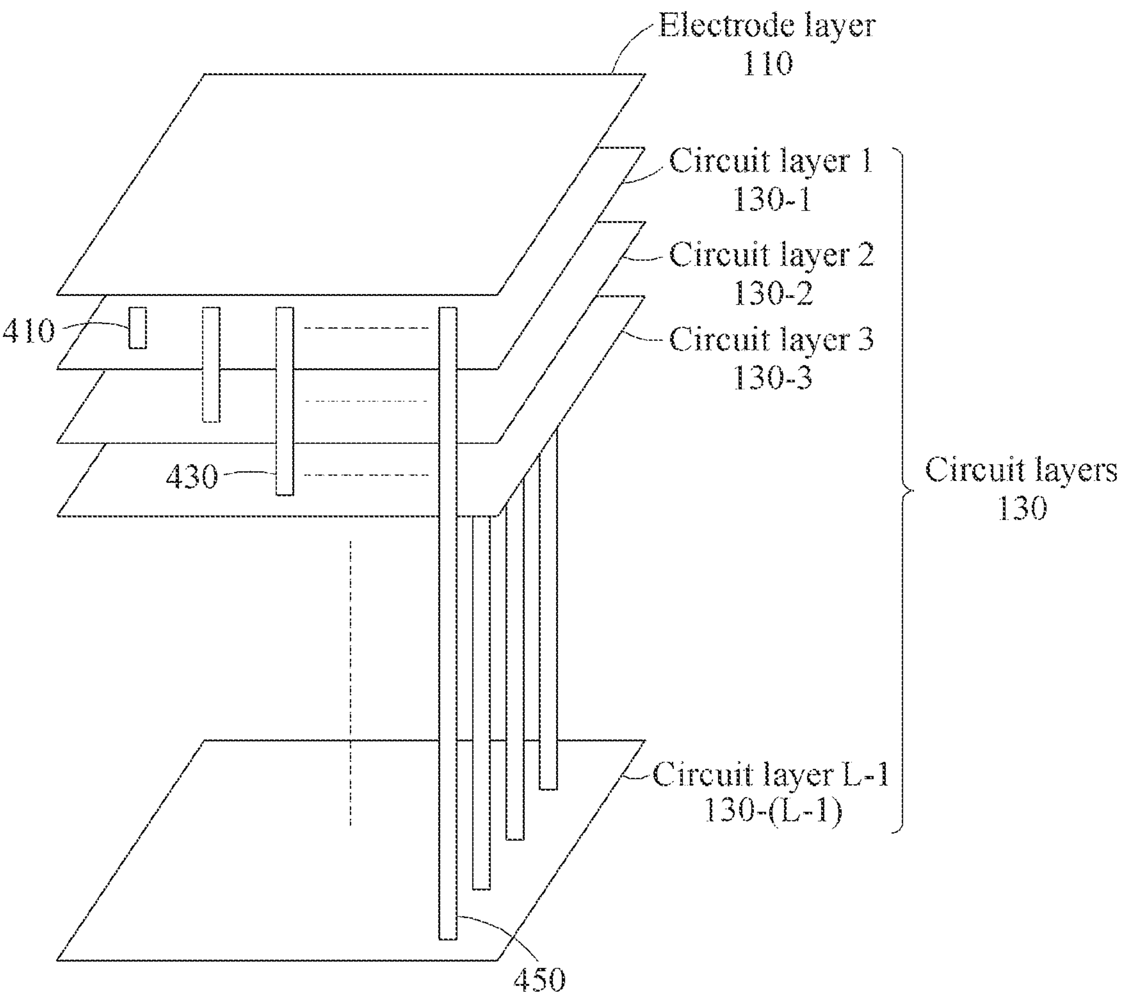

FIG. 4 illustrates an example of a method of connection between contiguous layers within a bioprocessing element. More specifically, FIG. 4 illustrates a connection method of inter-layer connectors 410, 430, and 450 when unit blocks of the circuit layer 130 performing a same function are disposed to different circuit layers.

Functionally contiguous unit blocks may not always be contiguously disposed physically in a circuit layer, according to examples. Here, "functionally contiguous unit blocks" may be understood as unit blocks that are to be connected together to perform a function or as necessary partial blocks to perform a function.

When the functionally contiguous unit blocks among the unit blocks are dispersed to different layers, the dispersed unit blocks may be interconnected through diverse connection types of the inter-layer connectors 410, 430, and 450 as shown in FIG. 4.

For example, when the functionally contiguous unit blocks are dispersed to different layers such as the circuit layer 1 130-1 and the circuit layer L−1 130-(L−1), the dispersed unit blocks may be interconnected through the inter-layer connector 450.

By dispersing the functionally contiguous unit blocks to different circuit layers, a size of the unit block included in one circuit layer may be increased and a total number of inter-layer connectors in use may be reduced.

Here, a thickness of the inter-layer connectors 410, 430 and 450 may vary, for example, based on a feature of a signal which is transmitted through the inter-layer connector(s) connecting the dispersed unit blocks, a position of layers on which the unit blocks are disposed wherein the layers are connected by the corresponding inter-layer connector(s), and/or a distance between layers connected by the corresponding inter-layer connector(s).

Figure 5:
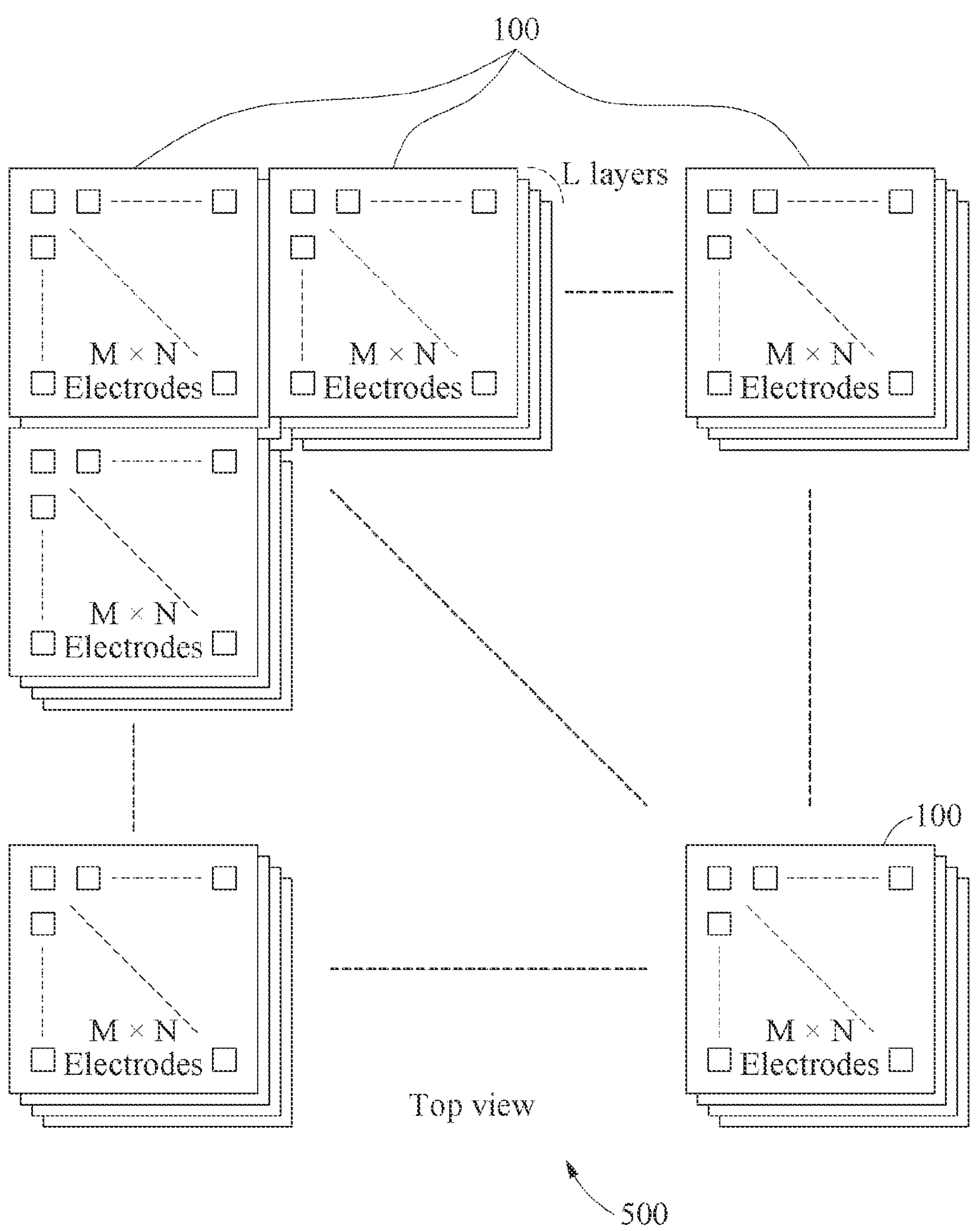
FIG. 5 illustrates an example of a structure of a neural network processor including a plurality of bioprocessing elements.

FIG. 5 illustrates an example of a structure of a neural network processor. More specifically, FIG. 5 illustrates a structure of a neural network processor 500 including a plurality of the bioprocessing elements 100.

The plurality of bioprocessing elements 100 included in the neural network processor 500 may be connected in parallel. The neural network processor 500 may secure or achieve infinite two-dimensional scalability by connecting the plurality of bioprocessing elements 100 in parallel, and here, the neural network processor 500 may measure signals of almost all biological neurons since a recording area is not sparse. Referring to FIGS. 1 to 4, a structure or operation of the plurality of bioprocessing elements 100 may be the above-described structure and operation of the bioprocessing element 100.

A disposition spacing between the plurality of bioprocessing elements 100 in the neural network processor 500 may be determined, for example, based on an energy density or an electrode density of electrodes included in the bioprocessing element 100. The neural network processor 500 may record and/or analyze neural signals of a large-scale neural network without an omission by expanding a recording area while maintaining the electrode density by maintaining tight disposition spacing between the plurality of bioprocessing elements 100.

The neural signals of the large-scale neural network may be recorded and analyzed without an omission by forming a three-dimensional brain recording platform which is expandable in real-time by plurally disposing the bioprocessing elements 100 in parallel and maintaining tight disposition spacing between the bioprocessing elements 100.

Although a plurality of bioprocessing elements is used in parallel when a signal of the large-scale neural network is measured, a number of biological neurons not in contact with an electrode and thus not measurable may be minimized by preventing an area of circuit layers from being sparse by stacking layers such that an area of each of the circuit layers may not exceed an area of an electrode layer.

For example, the neural network processor 500 may be a programming platform to record a functional map of a natural neural network. For example, the neural network processor 500 may extract action potential and post-synaptic potential in biological neurons by measuring membrane potential of each of the biological neurons from the bioprocessing elements 100 respectively in real-time. Here, the neural network processor 500 may cause a membrane permeability by transmitting faradaic current to the bioprocessing elements 100. The faradaic current may cause a gradual penetration of a cell membrane and may change a cell-electrode combination from outside biological neurons to inside biological neurons. The neural network processor 500 may explicitly map an entire network about an excitatory and/or inhibitory synaptic connection of a plurality of biological neurons recorded during a predetermined time through a network coverage of a neural network and parallel processing for recording in a cell.

The bioprocessing elements, electrode layers, electrodes, circuit layers, inter-layer connectors, unit blocks, blocks, block groups, connectors, neural network processors, bioprocessing element 100, electrode layer 110, electrodes 115, circuit layers 130, inter-layer connectors 150, circuit layer 201, circuit layer 203, unit blocks 205, block groups 210, 230, and 250, connectors 410, 430, and 450, neural network processor 500, and other apparatuses, units, modules, devices, and components described herein with respect to FIGS. 1-5 are implemented by or representative of hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 1-5 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions in the specification, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access programmable read only memory (PROM), electrically erasable programmable read-only memory (EEPROM), random-access memory (RAM), dynamic random access memory (DRAM), static random access memory (SRAM), flash memory, non-volatile memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, a card type memory such as multimedia card micro or a card (for example, secure digital (SD) or extreme digital (XD)), magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents.

What is claimed is:

1. A bioprocessing device performing an operation based on cultured biological neurons, the device comprising:

an electrode layer comprising electrodes configured to be connected to the biological neurons;

circuit layers, stacked with the electrode layer, comprising stacked circuits for the biological neurons, wherein, for each of the circuit layers, circuit blocks of different groups comprised in the circuit layer are configured to perform different predetermined functions and signals of circuit blocks of a same group comprised in the circuit layer performing a same predetermined function are grouped and transmitted to circuit blocks of a same group comprised in another one of the circuit layers configured to perform the same predetermined function; and inter-layer connectors configured to connect the electrode layer and the circuit layers.

2. The device of claim 1, wherein an area of each of the circuit layers is smaller than or equal to an area of the electrode layer.

3. The device of claim 1, wherein an area of the electrode layer is determined based on either one or both of a thickness of the inter-layer connectors and a number of the inter-layer connectors.

4. The device of claim 1, wherein any one or any combination of any two or more of a number of the electrodes, a number of the circuit layers, a circuit configuration of each of the circuit layers, and a method of connection between the circuit layers is determined based on an application field of the device.

5. The device of claim 1, wherein a disposition spacing between the electrodes is determined based on a size of the biological neurons.

6. The device of claim 1, wherein the inter-layer connectors comprise either one or both of:

through silicon vias (TSVs) penetrating the electrode layer and the circuit layers; and micro bumps connecting the electrode layer and the circuit layers.

7. The device of claim 1, wherein each of the circuit layers comprises circuit blocks configured to perform a predetermined function, and signals of the circuit blocks performing the same function among the circuit blocks comprised in the corresponding circuit layer are grouped into one group and transmitted.

8. The device of claim 7, wherein each of the circuit blocks comprises a circuit configured to perform a predetermined function.

9. The device of claim 7, wherein the circuit blocks performing the same function among the circuit blocks are contiguously disposed to each other.

10. The device of claim 1, wherein each of the circuit layers comprises circuit blocks configured to perform a predetermined function, and signals of at least a portion of the circuit blocks comprised in a corresponding circuit layer are grouped through circuits connected to the inter-layer connectors.

11. The device of claim 1, wherein each of the circuit layers comprises circuit blocks configured to perform a predetermined function, and one or more of the circuit blocks receives a signal from one or more of the electrodes.

12. The device of claim 1, wherein each of the circuit layers comprises circuit blocks configured to perform a predetermined function, and signals of at least a portion of the circuit blocks comprised in a corresponding circuit layer are grouped by any one or any combination of any two or more of a time division multiplexing method, a frequency division multiplexing method, and a code division multiplexing method.

13. The device of claim 1, wherein the circuit layers comprise circuit blocks configured to perform a predetermined function, and in response to functionally contiguous circuit blocks among the circuit blocks being dispersed to different circuit layers, the dispersed circuit blocks are interconnected by the inter-layer connectors.

14. The device of claim 1, wherein the device is configured to perform either one or both of stimulating the biological neurons and analyzing a neural signal of the biological neurons.

15. The device of claim 1, wherein the device is a bioprocessing element.

16. A neural network processor comprising a plurality of the bioprocessing device of claim 1, wherein the bioprocessing devices are connected in parallel.

17. A neural network processor comprising:

a plurality of bioprocessing devices performing an operation based on cultured biological neurons, wherein the bioprocessing devices are connected in parallel, and wherein each of the bioprocessing elements comprises:

an electrode layer comprising electrodes configured to be connected to the biological neurons;

circuit layers, stacked with the electrode layer, comprising stacked circuits for the biological neurons, wherein, for each of the circuit layers, circuit blocks of different groups comprised in the circuit layer are configured to perform different predetermined functions and signals of circuit blocks of a same group comprised in the circuit layer performing a same predetermined function are grouped and transmitted to circuit blocks of a same group comprised in another one of the circuit layers configured to perform the same predetermined function; and inter-layer connectors configured to connect the electrode layer and the circuit layers.

18. The processor of claim 17, wherein a disposition spacing between the bioprocessing devices is determined based on an electrode density of the electrodes.

19. The processor of claim 17, wherein each of the circuit layers comprises circuit blocks configured to perform a predetermined function, and signals of the circuit blocks performing the same function among the circuit blocks comprised in a corresponding circuit layer are grouped into one group and transmitted.

20. The processor of claim 17, wherein each of the circuit layers comprises circuit blocks configured to perform a predetermined function, and signals of at least a portion of the circuit blocks comprised in a corresponding circuit layer are grouped through circuits connected to the inter-layer connectors.

21. The processor of claim 17, wherein each of the circuit layers comprises circuit blocks configured to perform a predetermined function, and one or more of the circuit blocks is configured to receive a signal from one or more of the electrodes.

22. The processor of claim 17, wherein each of the circuit layers comprises circuit blocks configured to perform a predetermined function, and signals of at least a portion of the circuit blocks comprised in a corresponding circuit layer are grouped by any one or any combination of any two or more of a time division multiplexing method, a frequency division multiplexing method, and a code division multiplexing method.

23. The processor of claim 17, wherein the circuit layers comprise circuit blocks configured to perform a predetermined function, and in response to functionally contiguous circuit blocks among the circuit blocks being dispersed to different circuit layers, the dispersed circuit blocks are interconnected by the inter-layer connectors.

24. A bioprocessing device performing an operation based on cultured biological neurons, the device comprising:

an electrode layer comprising electrodes configured to be connected to the biological neurons;

a circuit layer stacked with the electrode layer and comprising groups of adjacent circuit blocks, wherein, for each of the groups, the circuit blocks of the group are configured to perform a same operation that is different than an operation performed by circuit blocks of another one of the groups and signals of the circuit blocks of the group are grouped and transmitted to circuit blocks of another group of another circuit layer configured to perform the same operation; and inter-layer connectors configured to connect the electrode layer and the circuit layer.

25. The device of claim 24, wherein circuit blocks of a first group of the groups are configured to perform a first operation, and circuit blocks of a second group of the groups are configured to perform a second operation.

26. The device of claim 25, wherein the first operation and the second operation correspond to different operations among measuring a neural signal of the biological neurons, processing the neural signal of the biological neurons, and providing a stimulus signal to the biological neurons.

* * * * *